US006610011B2

(12) United States Patent
Emery

(10) Patent No.: US 6,610,011 B2
(45) Date of Patent: Aug. 26, 2003

(54) METHOD AND SYSTEM FOR CONTROL OF PROBE HEATING USING LENS REFLECTION PULSE-ECHO FEEDBACK

(75) Inventor: Charles D. Emery, Renton, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 09/752,481

(22) Filed: Dec. 27, 2000

(65) Prior Publication Data

US 2002/0082501 A1 Jun. 27, 2002

(51) Int. Cl.[7] ................................................ A61B 8/00
(52) U.S. Cl. ...................................................... 600/437
(58) Field of Search ................................. 600/437, 443, 600/447; 601/2, 3; 604/22; 606/1

(56) References Cited

U.S. PATENT DOCUMENTS

| | | | |
|---|---|---|---|
| 4,603,702 A | * 8/1986 | Hwang et al. | ............... 600/437 |
| 4,708,127 A | * 11/1987 | Abdelghani | .................... 601/2 |
| 4,867,168 A | 9/1989 | Stoor et al. | |
| 4,945,797 A | 8/1990 | Hahn | |
| 5,107,837 A | 4/1992 | Ophir et al. | |
| 5,143,070 A | 9/1992 | Ophir et al. | |
| 5,178,147 A | 1/1993 | Ophir et al. | |
| 5,247,937 A | 9/1993 | Ophir et al. | |
| 5,293,870 A | 3/1994 | Ophir et al. | |
| 5,396,891 A | * 3/1995 | Whitney et al. | ............ 600/449 |
| 5,474,070 A | 12/1995 | Ophir et al. | |
| 5,552,645 A | * 9/1996 | Weng | .......................... 307/117 |
| 5,638,820 A | 6/1997 | Chen et al. | |
| 5,654,509 A | 8/1997 | Miele et al. | |
| 5,721,463 A | 2/1998 | Snyder | |
| 5,826,578 A | * 10/1998 | Curchod | ...................... 434/252 |
| 6,176,840 B1 | * 1/2001 | Nishimura et al. | ............. 601/2 |
| 6,183,426 B1 | * 2/2001 | Akisada et al. | ................. 601/2 |

OTHER PUBLICATIONS

U.S. patent application Ser. No. 09/522,985, Silwa, Jr. et al., filed Mar. 10, 2000.
Compatibility of Varian 2100C gated operations with enhanced dynamic wedge and IMRT dose delivery, Med. Phys., Aug. 2000.
"Image of the Elastic Properties of Tissue—A Review", L. Gao, K.J. Parker, R.M. Lerner, S.F. Levinson, Ultrasound in Med. & Biol., vol. 22, No. 8, pp. 959–977, 1996.

* cited by examiner

*Primary Examiner*—Francis J. Jaworski

(57) ABSTRACT

A method and system for controlling probe heating in an ultrasound system is disclosed. The method and system comprises electrically exciting a transducer within the probe; and detecting at least one pulse characteristic from the excited transducer. The method and system further includes analyzing at least one pulse characteristic to determine if the probe is coupling into a reflecting medium such as air or into tissue. Accordingly, a system and method in accordance with the present invention detects when an ultrasound transducer is coupling energy into a patient or into a reflecting medium such as air. In so doing, the thermal performance of the transducer improves by allowing an increase in the duration and level of the transducer excitation voltage.

31 Claims, 5 Drawing Sheets

METHOD AND SYSTEM FOR CONTROL OF PROBE HEATING USING LENS REFLECTION PULSE-ECHO FEEDBACK

FIELD OF THE INVENTION

The present invention relates to ultrasounds systems and more particularly to control of probe heating in such systems.

BACKGROUND OF THE INVENTION

Ultrasound is an increasingly used tool for noninvasively examining the human body. Diagnostic ultrasound is routinely used to examine a beating heart, diagnose valve abnormalities, monitor fetal growth, and detect lesions in the liver. Furthermore, ultrasound is commonly used to diagnose regions of atherosclerosis by measuring blood flow.

A typical ultrasound system works by transmitting high frequency acoustic signals into the body using a piezoelectric transducer. The ultrasound transducer converts electrical energy into mechanical energy (ultrasonic wave) that propagates into the body. The ultrasonic wave propagates in the body and is scattered, absorbed and reflected by various tissues. The ultrasound echo that is directed back to the piezoelectric transducer is converted from mechanical energy back to electrical energy. The ultrasound echo strength is detected and is typically used to modify the intensity of pixels in a digital display screen to create an image of the tissue in the body.

Ultrasound transducers typically include the following materials: backing, PZT, matching layers and a lens. In some system modes, the transmit voltage to the PZT is decreased because of the power dissipation within the ultrasonic transducer. The power is dissipated in the various transducer materials depending on the loss mechanism. The absorbed power causes heating of the probe that may be unacceptable to patient comfort or material thermal tolerances. Other designs may also convert the electrical to mechanical energy such as capacitive membrane ultrasonic transducers. These transducers also experience thermal limitations.

Ideally, the majority of power to a transducer dissipates in the human body and not the various transducer materials during transmit. The human body actually acts as a "heat sink" pulling transmit power away from the transducer. Of course, some of the power from the transducer is reflected and scattered back towards the transducer allowing images to be formed. Unfortunately, when the transducer is not transmitting into the body, some of the power is dissipated in the transducer materials causing probe heating. This transducer heating restricts the amount of transmit voltage during imaging. Therefore, the transducer loses transmit sensitivity because the system does not detect when the transducer is coupling into human soft tissue or air. Accordingly, what is needed is a system and method for overcoming the above-identified problems. The method and system should be cost-effective, compatible with existing systems and easily implemented on such systems. The present invention addresses such a need.

SUMMARY OF THE INVENTION

A method and system for controlling probe heating in an ultrasound system is disclosed. The method and system comprises electrically exciting a transducer within the probe; and detecting at least one pulse characteristic from the excited transducer. The method and system further includes analyzing at least one pulse characteristic to determine if the probe is coupling into a reflecting medium such as air or into tissue.

Accordingly, a system and method in accordance with the present invention detects when an ultrasound transducer is coupling energy into a patient or into a reflecting medium such as air. In so doing, the thermal performance of the transducer improves by allowing an increase in the duration and level of the transducer excitation voltage.

DETAILED DESCRIPTION

The present invention relates to ultrasound systems and more particularly to control of probe heating in such systems. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiment shown but is to be accorded the widest scope consistent with the principles and features described herein.

Figure 1:
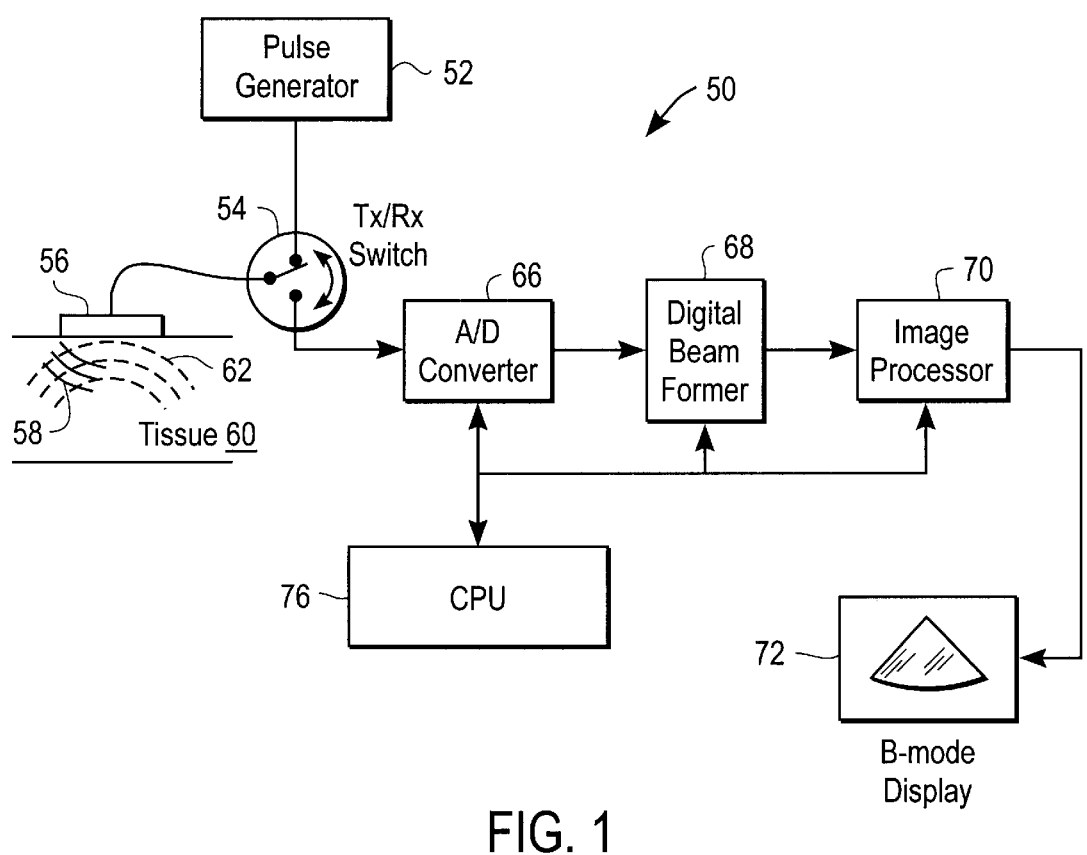
FIG. 1 is a simplified block diagram of an ultrasound system according to the present invention.

FIG. 1 is a simplified block diagram of an ultrasound system according to the present invention. The ultrasound system 50 includes a pulse generator 52 that generates a series of electronic signals that are optimized to excite the ultrasonic transducer 56. The output of the pulse generator 52 is fed to a transmit/receive switch 54 that has two positions. In the first position, the output of the pulse generator is coupled to an ultrasonic transducer 56. In the second position, the signals produced by the transducer in response to a received echo are coupled to an analog-to-digital converter 66.

The ultrasonic transducer 56 comprises an array of transducer elements, each of which is a piezoelectric crystal that converts the electronic signal into an ultrasonic wave 58 that is directed into the tissue of the patient 60. An ultrasound echo 62 is scattered and reflected off the internal body matter of the patient and is received by the ultrasonic transducer 56. Upon receiving the ultrasound echo, the transducer elements generate electronic signals that are analyzed by the ultrasound system to produce the ultrasound image.

With the transmit/receive switch 54 in the second position, the output signals produced by the ultrasonic transducer 56 are coupled to the analog-to-digital converter 66. The analog-to-digital converter converts the received echoes from a continuous analog signal to a discrete digital signal. The output of the analog-to-digital converter 66 is fed to a digital beam former 68 that combines the digitized signals from each of the transducer elements into a single binary number that is representative of the echo intensity at any given position in the tissue 60. The output of the digital beam former is fed to an image processor 70 which produces a digital ultrasound image that is in turn displayed on a display screen 72.

Controlling the operation of the ultrasound system 50 is a central processing unit 76 having its own internal memory in which data and the operating instructions for the CPU are stored. In addition, the CPU 76 may be coupled to a mass storage device such as a hard drive, a communication circuit for transmitting and receiving data from a remote location and a video tape recorder for recording the ultrasound images produced.

Figure 2:
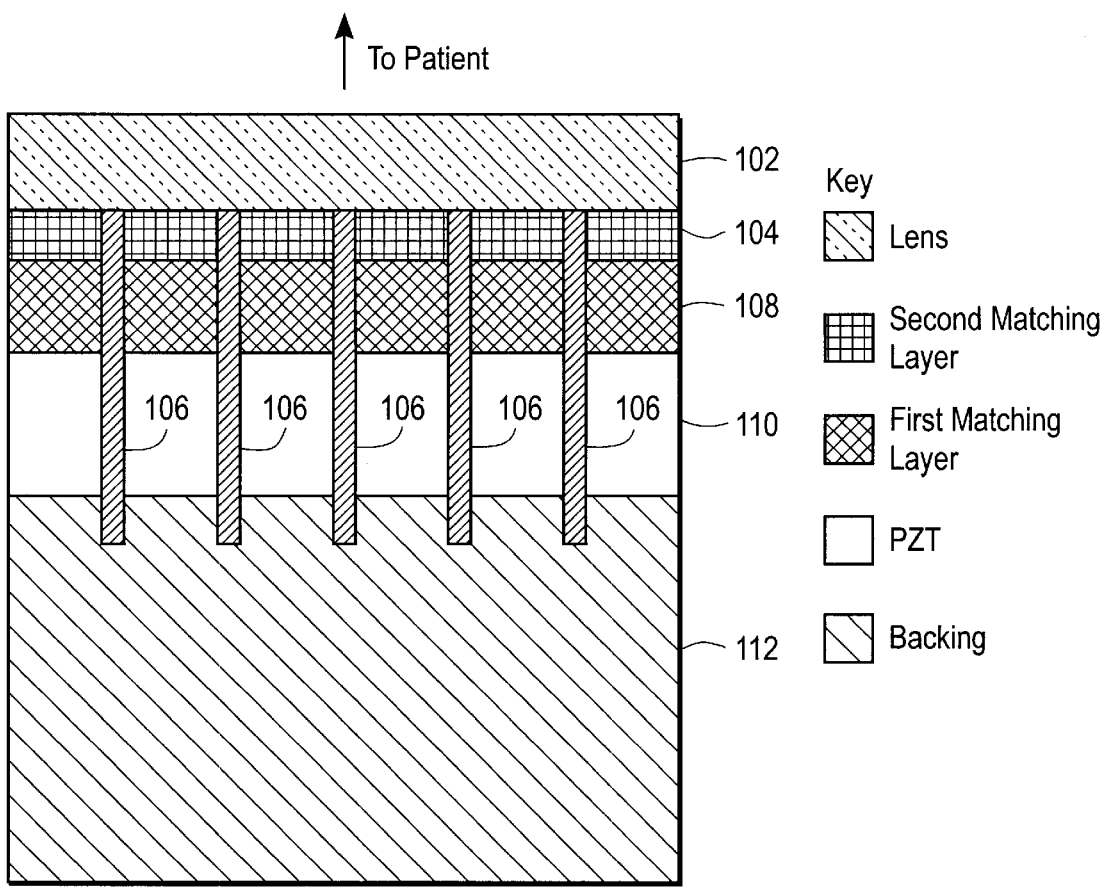
FIG. 2 shows a cross-section of several elements within a PZT based ultrasound transducer.

FIG. 2 shows a cross-section of several elements within an ultrasound transducer 56. The elements include a lens 102 which is mechanically coupled to a first matching layer 104. A second matching layer 108 is mechanically coupled to the first matching layer 104. The PZT 110 is converts the electrical signal to the mechanical wave. The ultrasound transducer 56 is typically used to image various organs within the human body such as the heart, kidneys or liver.

During transmit, a voltage pulse from the pulse generator 52 excites the transducer elements 106 within the ultrasound transducer 56 causing the PZT 110 to mechanically vibrate. The mechanical energy is coupled to the patient through matching layers 104 and 108 and a lens 102. Unfortunately, not all of the electrical energy is converted into mechanical energy. Some of the electrical energy is dissipated within the PZT element 110 because of mechanical and dielectric losses. Furthermore, some of the mechanical energy is coupled into the backing 112 or damped within the matching layers elements 104 and 102 and lens 102. These loss mechanisms cause excessive heating of the array of transducer 106 and limit the duration and level of excitation voltage that can be used to excite the transducers elements 106.

When the transducer 56 is not coupled to the tissue 60 but a nonabsorbing medium such as air and the transducer elements 106 are still excited, the majority of the energy that was coupled into the patient is reflected back towards the ultrasound transducer 56 from the lens 102/air interface to be reabsorbed. Again some of the energy is dissipated in the lens 102, matching layers 104 and 108, backing 112 and PZT element 110 causing further heating.

Low energy coupled into air implies that the majority of the energy is absorbed in the transducer. The pulse-echo response also provides information about the reflected pulse from the lens/air interface. The reflected pulse will be:

1. Extremely high in amplitude.
2. Have a long pulse length.
3. Occur immediately after the transmit burst.

Accordingly, a system and method in accordance with the present invention detects when the ultrasound transducer is coupling energy into soft tissue 60 or into the air and deactivates the probe when the probe is coupling energy into air. In so doing, the thermal performance of the transducer improves allowing an increase in the duration and level of excitation voltage used from the pulse generator 52.

If this type of pulse is detected with the above characteristics, a system is utilized to reduce the transmit voltage to decrease the chance of probe heating. Ultimately, this means the probe could run at a higher transmit voltage when coupled into the tissue because of less thermal heating when the probe is coupled into air. To describe this feature in more detail, refer now to the following illustration in conjunction with the figure.

Although the present invention will be described in the context of a PZT element, other materials could be utilized as a transducer and their use would be within the spirit and scope of the present invention. For example, capacitive membrane ultrasonic transducers (CMUTs) produced via micro electromechanical systems (MEMs) techniques, could be utilized and those type of transducers may have similar or more extensive problems. Accordingly, a system and method in accordance with the present invention could be used with a variety of materials.

Figure 3A:
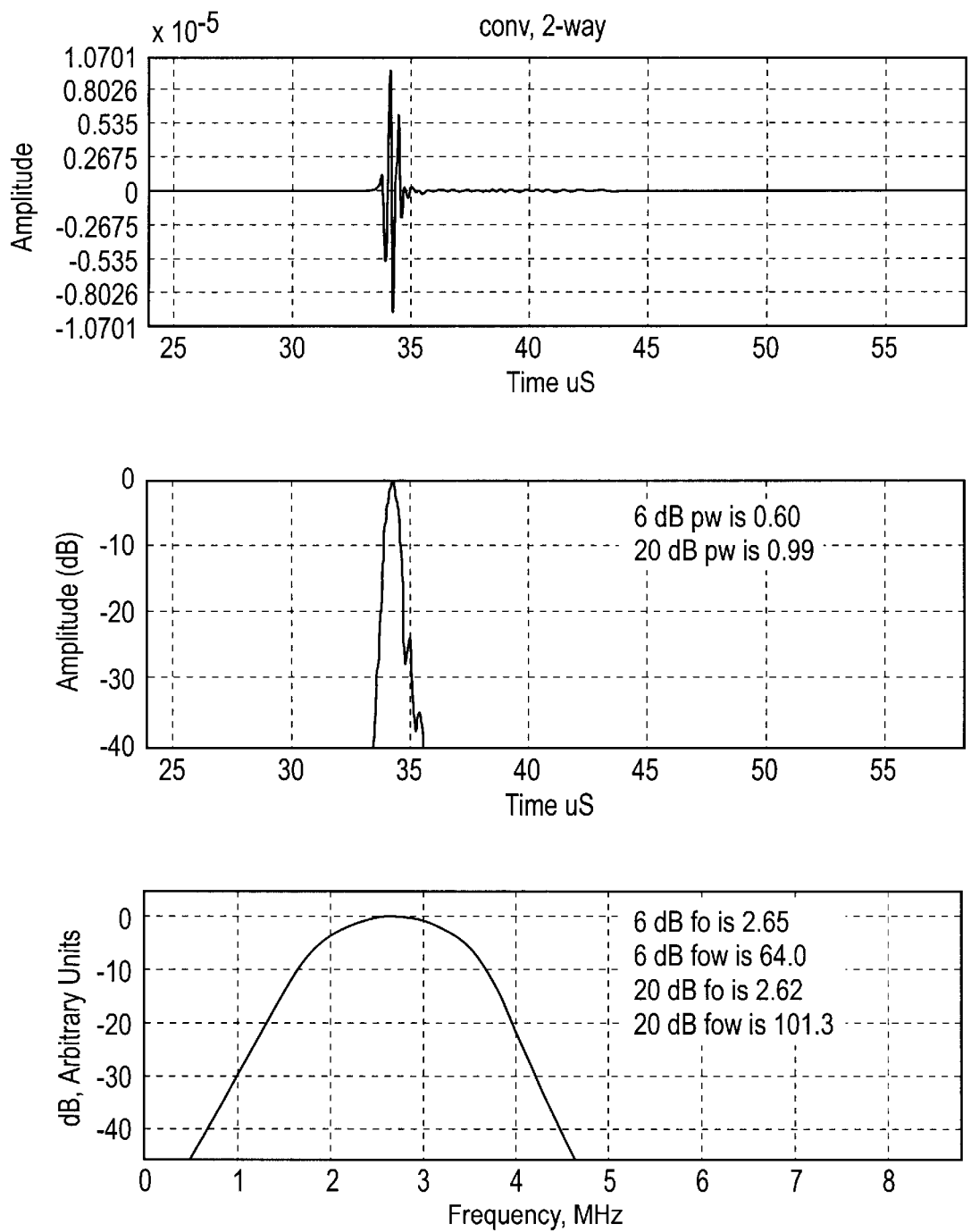
FIG. 3a shows the initial pulse-echo response from a lens that is coupled into a fat layer.
Figure 3B:
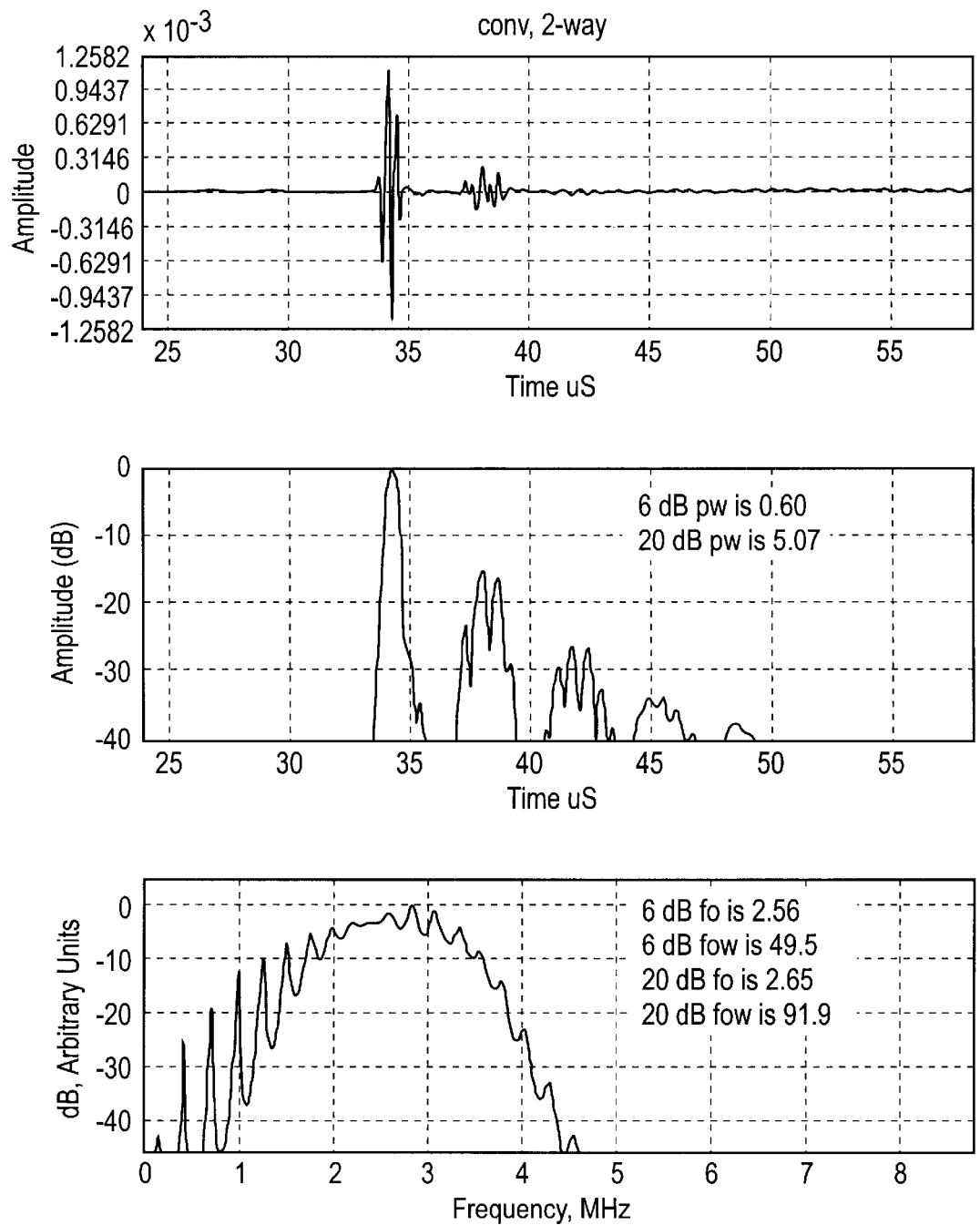
FIG. 3b shows that the initial pulse-echo response changes significantly if the same array element is coupled into air.

FIG. 3a shows the initial pulse echo response from a lens that is coupled into a fat layer. The pulse was obtained using a model as described in "New equivalent circuits for elementary piezoelectric transducers," in Electronic Letters, vol. 6, no. 13, pp. 398–399 by Krimholtz, R., Leedom, D. A., and Matthaii, G. L. The lens impedance is assumed to be 1.5 MRayls and the fat layer has an impedance of 1.45 MRayls. If the same array element is coupled into air, the pulse-echo response changes significantly as shown in FIG. 3b. The pulse rings more because of continuous reflections off of the lens/air interface 102 (FIG. 2). The pulse amplitude has also dramatically changed. The significant differences in the pulse response allows specific time windows and spectral based algorithms to be used to detect when the transducer is coupling energy into air. Overall, the initial peak-to-peak amplitude of the pulse in air is approximately 42 dB higher than the pulse coupled into fat.

FIGS. 3a and 3b also show the characteristics in pulse shape between an element coupled to air and an element coupled to tissue. The first major difference is the pulse amplitude, which differs by approximately 40 db. This is the primary pulse characteristic of a transducer coupled into air. Furthermore, the echo occurs almost instantly after the transmit pulse. The air coupled transducer also has multiple echoes from the lens/air interface. The pulse amplitude decreases by approximately 15 dB for each echo due to energy absorbed in the lens, backing, matching layers, PZT and at the A/D converter.

In a preferred embodiment, a general testing procedure is utilized to provide the detection of whether the transducer is transmitting in air or into tissue. This procedure could be implemented in an algorithm which is part of a computer program. The program can be implemented in computer readable medium within the CPU 76. The computer readable medium can be implemented in a disk drive, floppy drive, CD-ROM, DVD or the like.

Figure 4:
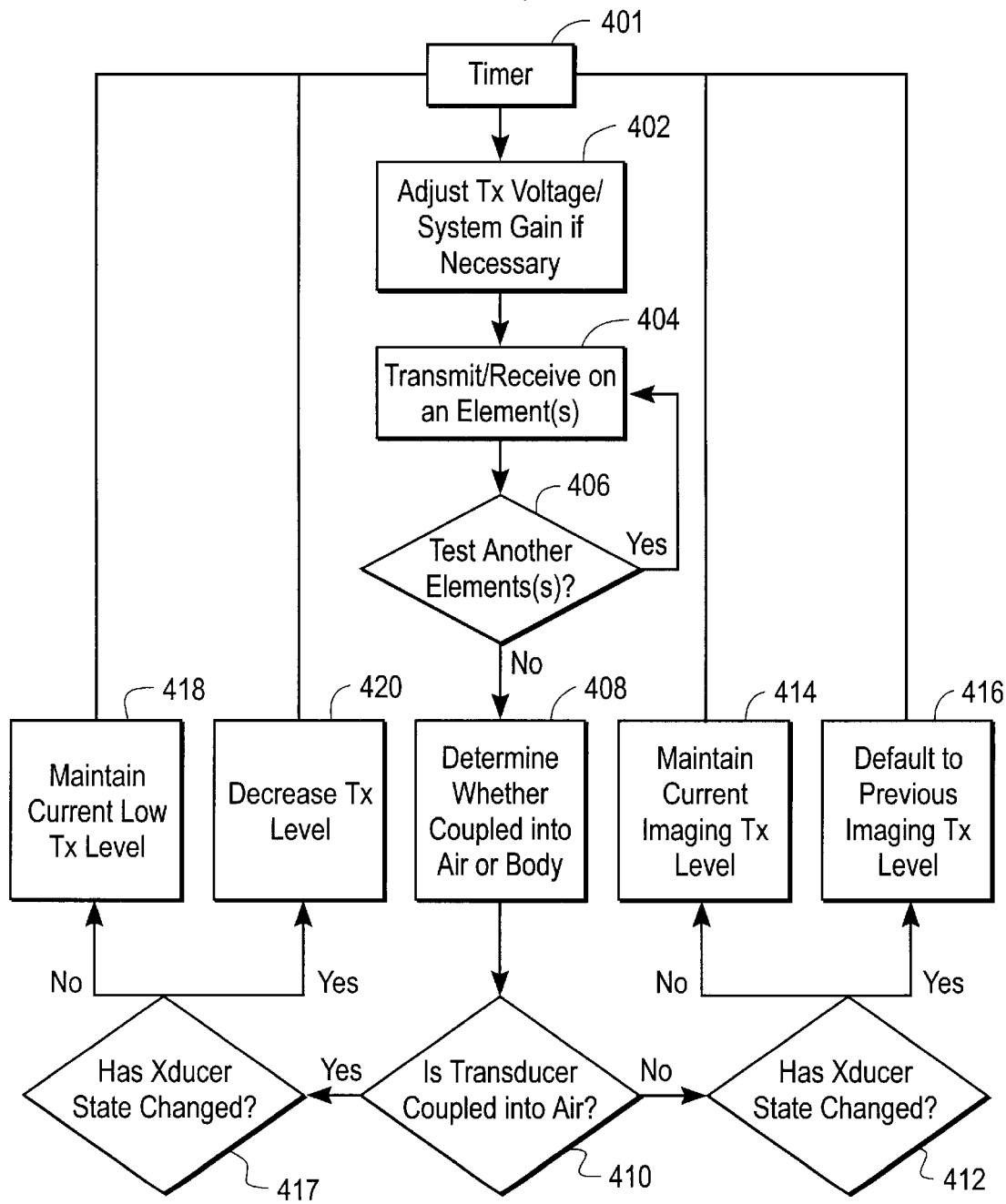
FIG. 4 shows a flow chart illustrating a testing process for determining if the transducer is coupled into air or tissue.

FIG. 4 is a flow chart that illustrates a testing process for determining if the transducer is coupled into air or into tissue. Because of the short time required to perform the test, the process should be applied at various times during imaging. A system timer 401 is used to determine when the process is used. The timer 401 may vary depending on the current state of the transducer. For example, if the transducer is in air, then the tests may occur much more frequently.

Accordingly, when the timer 401 first initiates the use of the process, the transmit voltage and overall receive gain is adjusted for the probe type, via step 402. For example, many probes have different acoustical/electrical characteristics that will require different transmit voltages to be used.

After the transmit voltage and receive gain are adjusted, the transducer element or elements are electrically excited, via step 404. Next, the receive waveform over the same transmit element(s) or different element(s) are captured for a specific amount of time, via step 406. The response of all of the transducer elements or a select few elements at various locations can be utilized across the transducer face. Lens thickness and velocity determine the time window of interest.

After the required elements have been tested, one or a combination of the following pulse characteristics may be used to determine if the element is coupling into air or tissue, via step 408. The pulse characteristics are for example:

peak-to-peak level of rf pulse-echo signal peak-to-peak level of detected pulse-echo signal time of occurrence spectral shape The determining step 408 could analyze the pulse in one or more of the following ways.

In a first embodiment, the step could be determined if a high amplitude pulse is transmitted over a specific period of time. In a preferred embodiment, adjustment would also be made if coupling gel is placed on the transducer. The coupling gel would change the time when the echo occurs; however, amplitude would remain much higher than a transducer coupled to tissue. This amplitude method could also be applied to the envelope detected rf pulse.

In another embodiment, a pulse envelope could be analyzed to determine whether the transducer array is coupled into air or tissue. However, this is more computationally intensive and may be less robust. As shown in FIG. 3b, the air-coupled transducer has multiple pulses due to reflection off of the lens and transducer stack. The pulses tend to decrease by approximately ~15 db each time. Therefore, comparing the amplitude of the first pulse to the second pulse suggests whether the transducer is coupled into air or tissue.

In another embodiment, the pulse spectrum could be analyzed. The multiple reflections give rise to peaks in the pulse-echo spectrum of the rf pulse. The distance between the reflections determines the frequency between the peaks in the pulse-echo spectrum. Taking the derivative of the pulse spectrum determines the location of the peaks. If the peaks occur at a specific frequency period that can be matched to the lens thickness, then the probe may be coupled into air if the peaks have a specific amplitude. An amplitude threshold may then be set to determine if the spectral peaks are large enough to consider the transducer to be coupled into air.

Referring back to FIG. 4, next, a specific number of elements must meet these criteria to decide if the entire probe is coupled into air or tissue, via step 410. If the results indicate the transducer is coupled into tissue, then the system must know what the previous state of the system is, via step 412. If previously, the transducer was coupled into tissue, then the same imaging transmit levels are maintained, via step 414. If previously the transducer was coupled into air and now it is coupled to tissue, then the system should default to the previous imaging transmit level, via step 416.

Next, suppose the results suggest the transducer is coupled into air. Again the previous state of the transducer must be determined, via step 417. If previously the transducer was coupled into air, then the current low transmit level is maintained, via step 418. However, if the probe was previously imaging and the transducer is now coupling into air, then the transmit level is reduced, via step 420.

Additional control mechanisms may be added to the system or probe to determine whether a probe is in use. The additional mechanisms may be used separately or in conjunction with the algorithm stated above for increased accuracy. For example, electro-optical or electromechanical or physical switches added to the probe holder on the system notifies the system if the probe has been picked up by the user. Furthermore, sensors in the probe may detect when the probe is in use. The sensors may include:

(1) motion detectors (2) optical emitter/detector pairs (3) thermal sensors

The motion detector would simply detect movement of the probe, which primarily occurs during scanning. An optical emitter/detector pair would sense the amount of light reflected by the tissue. Obviously, both techniques could be used separately or in combination with the process shown in FIG. 4 to reduce the transmit power to the probe elements. By regulating the transmit voltage to the elements, the transmit sensitivity as well as the probe life and reliability are increased.

Accordingly, a system and method in accordance with the present invention detects when an ultrasound transducer is coupling energy into tissue or into the air. In so doing, the thermal performance of the transducer improves allowing an increase in the duration and level of excitation voltage used to transmit energy.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A method for controlling probe heating in an ultrasound system comprising the steps of:

(a) determining if a probe is coupled to a body to be imaged, the determination being in response to a transmitted pulse and an echo response from a lens of the probe; and (b) changing from an imaging voltage amplitude of the probe if the probe is not coupled to a body to be imaged.

2. The method of claim 1 wherein the determining step (a) further comprises the steps of:

(a1) exciting a transducer within the probe;

(a2) detecting at least one pulse characteristic from the excited transducer; and (a3) analyzing the at least one pulse characteristic to determine if the probe is coupling into a reflecting medium or into a tissue.

3. A method for controlling probe heating in an ultrasound system comprising the steps of:

(a) determining if a probe is coupled to a body to be imaged, the determination being in response to a transmitted pulse and the determination being in response to a plurality of pulse characteristics detected in response to the transmitted pulse; and (b) changing from an imaging voltage amplitude if the probe is not coupled to a body to be imaged.

4. The method of claim 3 wherein the plurality of pulse characteristics include any combination of peak to peak level of a pulse echo, time of occurrence and spectral shape of the pulse.

5. The method of claim 2 wherein the analyzing step (a3) comprises the step of:

(a31) determining if a high amplitude pulse is transmitted over a predetermined period of time.

6. A method for controlling probe heating in an ultrasound system comprising the steps of:

(a) determining if a probe is coupled to a body to be imaged, the determination being in response to a transmitted pulse and a function of an envelope of an echo response pulse; and (b) changing from an imaging voltage amplitude of the probe if the probe is not coupled to a body to be imaged.

7. The method of claim 2 wherein the analyzing step (a3) comprises the step of:

(a31) analyzing a spectrum of the pulse.

8. The method of claim 2 which includes the step of:

(c) determining if the probe is in use.

9. A method for controlling probe heating in an ultrasound system comprising the steps of:

(a) determining if a probe is coupled to a body to be imaged, the determination being in response to a transmitted pulse;

(b) changing from an imaging voltage amplitude of the probe if the probe is not coupled to a body to be imaged; and (c) utilizing sensors to detect when the probe is in use.

10. The method of claim 9 wherein the sensors comprise motion detectors.

11. The method of claim 9 wherein the sensors comprise optical emitter/detector pairs.

12. The method of claim 2 wherein the analyzing step (a3) comprises:

(a31) determining if the results of the detecting step indicate that the transducer is coupled to tissue or into a reflecting medium;

(a32) determining the previous state of the transducer;

(a33) maintaining a low transmit level if the transducer was previously coupled to a reflecting medium and the results indicate that the transducer is coupled to a reflecting medium; and (a34) decreasing the transmit level to the transmit level if the probe was previously imaging and the transducer is coupled to a reflecting medium.

13. The method of claim 2 wherein the analyzing step (a3) comprises:

(a31) determining if the results of the detecting step indicate that the transducer is coupled to tissue or into a reflecting medium;

(a32) determining the previous state of the transducer;

(a33) maintaining an imaging transmit level if the transducer was previously coupled to tissue and the results indicate that the transducer is coupled to the tissue; and (a34) increasing the transmit level to the imaging transmit level if the probe was previously coupled into a reflecting medium and the transducer is now coupling into tissue.

14. The method of claim 1 wherein the probe is reactivated if the probe is inactive and the probe is again coupled to the body to be imaged.

15. A system for controlling probe heating in an ultrasound system comprising:

means for determining if a probe is coupled to a body to be imaged in response to a transmitted pulse and an echo response from a lens of the probe; and means for changing from an imaging voltage amplitude if the probe is not coupled to a body to be imaged.

16. The system of claim 15 wherein the determining means further comprises:

means for exciting the transducer within the probe;

means for detecting at least one pulse characteristic from the excited transducer; and means for analyzing the at least one pulse characteristic to determine if the probe is coupling into a reflecting medium or into tissue.

17. The system of claim 16 wherein the analyzing means comprises:

means for determining if a high amplitude pulse is transmitted over a predetermined period of time.

18. A system for controlling probe heating in an ultrasound system comprising:

means for determining if a probe is coupled to a body to be imaged, the determination being in response to a transmitted pulse and a function of an envelope of an echo response pulse; and means for changing from an imaging voltage amplitude of the probe if the probe is not coupled to a body to be imaged.

19. The system of claim 16 wherein the analyzing means comprises:

means for analyzing a spectrum of the pulse.

20. A system for controlling probe heating in an ultrasound system comprising:

means for determining if a probe is coupled to a body to be imaged, the determination being in response to a transmitted pulse;

means for changing from an imaging voltage amplitude of the probe if the probe is not coupled to a body to be imaged; and means for analyzing if the probe is in use.

21. The system of claim 20 wherein the determining means comprises means for utilizing sensors to detect when the probe is in use.

22. The system of claim 21 wherein the sensors comprise motion detectors.

23. The system of claim 21 wherein the sensors comprise optical emitter/detector pairs.

24. The system of claim 16 wherein the analyzing means comprises:

means for determining if the results of the detecting step indicate that the transducer is coupled to tissue or into a reflecting medium;

means for determining the previous state of the transducer;

means for maintaining a low transmit level if the transducer was previously coupled to a reflecting medium and the results indicate that the transducer is coupled to a reflecting medium; and means for decreasing the transmit level to the transmit level if the probe was previously imaging and the transducer is coupled to air.

25. The system of claim 16 wherein the analyzing means comprises:

means for determining if the results of the detecting step indicate that the transducer is coupled to tissue or into a reflecting medium;

means for determining the previous state of the transducer;

means for maintaining an imaging transmit level if the transducer was previously coupled to tissue and the results indicate that the transducer is coupled to the tissue; and means for increasing the transmit level to the imaging transmit level if the probe was previously coupled into a reflecting medium and the transducer is now coupled into tissue.

26. The system of claim 15 wherein the probe is reactivated if the probe is inactive and the probe is again coupled to the body to be imaged.

27. A system for controlling probe heating in an ultrasound system comprising:

a means for determining if a probe is coupled to a body to be imaged, the determination being in response to a transmitted pulse and the determination being in response to a plurality of pulse characteristics detected in response to the transmitted pulse; and means for changing from an imaging voltage amplitude if the probe is not coupled to a body to be imaged.

28. The system of claim 27 wherein the plurality of pulse characteristics include any combination of peak to peak level of a pulse-echo, time of occurrence and spectral shape of the pulse.

29. A computer readable medium containing program instructions for controlling probe heating in an ultrasound system, the program instructions comprising:

(a) determining if a probe is coupled to a body to be imaged in response to a pulse echo from a lens of the probe; and (b) deactivating the probe if the probe is not coupled to a body to be imaged.

30. The computer readable medium of claim 29 in which the program instructions include:

(a1) exciting the transducer within the probe;

(a2) detecting at least one pulse characteristic from the excited transducer; and (a3) analyzing the at least one pulse characteristic to determine if the probe is coupling into a reflecting medium or into tissue.

31. A method for controlling probe heating in an ultrasound system comprising the steps of:

(a) determining if a probe is coupled to a body to be imaged, the determination being in response to a transmitted pulse and based on a time of occurrence characteristic of an echo response pulse; and (b) changing from an imaging voltage amplitude of the probe if the probe is not coupled to a body to be imaged.

* * * * *